United States Patent [19]

Tuompo et al.

[11] Patent Number: 5,420,017

[45] Date of Patent: May 30, 1995

[54] METHOD AND KIT FOR THE DETECTION OF MICROORGANISMS

[75] Inventors: Helena Tuompo; Heljä Glasin, both of Epsoo, Finland

[73] Assignee: Orion Corporation Ltd., Finland

[21] Appl. No.: 740,320

[22] Filed: Aug. 5, 1991

[30] Foreign Application Priority Data

Jan. 24, 1991 [FI] Finland .................................. 910358
Jan. 24, 1991 [FI] Finland .................................. 910359

[51] Int. Cl.$^6$ .......................... C12M 1/12; C12N 1/02
[52] U.S. Cl. .......................................... 435/29; 435/4; 435/30; 435/34; 435/39; 435/261; 435/243; 435/311; 435/26; 252/DIG. 1
[58] Field of Search ....................... 435/29, 30, 34, 39, 435/311, 4, 261, 243, 26; 252/DIG. 1

[56] References Cited

U.S. PATENT DOCUMENTS 4,225,669 9/1980 Melnick ................................ 435/39

FOREIGN PATENT DOCUMENTS 0107594 7/1988 European Pat. Off. .

OTHER PUBLICATIONS

Michal, G. et al., "Methods in Enzymatic Analyses," vol. 1, pp. 197–232 (1983).
"Oxireductases," Histological and Histochemical Methods, Theory and Practice, 2d Ed., Chapter 16, pp. 258–287 (1990).
Baker et al., "Action of Synthetic Detergents on the Metabolism of Bacteria," J. Ex. Med., 73, pp. 249–271 (1941).
Dakay et al., "The Effect of the Synthetic Detergents on the Formazan Formation of Various Environmental Bacteria," Zbl. Bakt. Hyg., 1 Abt. Orig. B. 174 pp. 121–125 (1981).

*Primary Examiner*—William H. Beisner
*Assistant Examiner*—Jane Williams
*Attorney, Agent, or Firm*—Braumbaugh, Graves, Donohue & Raymond

[57] ABSTRACT

The presence of microorganisms in a liquid sample can be determined by a method comprising the steps of (a) filtering the liquid sample through a filter having a pore size which is small enough to prevent passage of microorganisms through the filter but large enough to permit passage of any free reducing agents present in the sample whereby microorganisms present in the sample are retained on the filter; (b) passing a test solution comprising a chromogenic reagent through the filter having the retained microorganisms thereon, said chromogenic reagent having an oxidation potential such that the reagent can be reduced by microbial dehydrogenase and said chromogenic reagent being selected such that reduction of the chromogenic reagent yields a visibly colored product; and (c) monitoring the filter for the formation of a visibly colored product, wherein the formation of a visibly colored product is indicative of the presence of microorganisms in the sample. This method can be practiced with the aid of a kit which comprises a filter apparatus, a test solution for visualization of microorganisms and optionally a solution of a non-ionic alkyl glucoside-type detergent and a chaotropic agent for visualization only gram-negative bacteria.

18 Claims, 1 Drawing Sheet

METHOD AND KIT FOR THE DETECTION OF MICROORGANISMS

BACKGROUND OF THE INVENTION

This application relates to a method and test kit for the detection of microorganisms in a liquid sample. The invention relies upon the ability of microbial dehydrogenase enzymes to reduce certain materials to produce visibly colored and therefore detectable products and capitalizes on this ability to produce simple and reliable kits to detect microorganisms such as bacteria generally or just gram negative bacteria.

It has long been recognized that dehydrogenases in living cells can be localized by histochemical methods within leucocytes and histological tissue sections by replacing the natural hydrogen acceptor with a reducible material, such as nitroblue tetrazolium as a ditetrazolium chloride, having a colored, water insoluble reduction product. Michel, G. et al. Methods in Enzymatic Analyses, Vol. 1, pp. 197-232 (1983). A similar approach has been used to detect living bacteria by observing whether a color change occurs upon the addition of a material such as triphenyl tetrazolium chloride (TTC), methylthiazolyldiphenyl tetrazolium bromide (MTT), iodonitrotetrazolium (INT) or neotetrazolium chloride (NTC), all of which turn red upon reduction, or blue tetrazolium (BT) or nitroblue tetrazolium (NBT) which turn blue upon reduction. Histological and Histochemical Methods, Theory and Practice, 2d. Ed. Chapter 16, p. 258 (1990).

The ability of living cells to reduce tetrazolium salts has formed the basis of a research tool to investigate the effects of various materials on bacterial respiration, i.e., oxygen uptake. In this regard, it has been reported that anionic detergents such as Tergitol-7 selectively inhibit the respiration of Gram-negative bacteria and consequently the reduction of tetrazolium salts to colored products. Cationic detergents inhibit respiration of both Gram-negative and Gram-positive bacteria, whereas neutral, non-ionic detergents are reported to have no effect on respiration. Baker et al., J. Exp. Med. 73, pp. 249-271 (1941). Dehydrogenase activity appears to be inhibited as well. Dakay et al., Zentralblatt Bakt. Hyg. I. Abt. Orig. B. 174, pp. 121-124 (1981).

The differential effects of detergents on dehydrogenase activity has been used as the basis for identifying bacterial types in liquid samples. European Patent Application 107594. It is an object the present invention to further exploit this ability of living bacteria and provide a method and test kit for simple and rapid determination of total microorganisms and Gram-negative bacteria.

SUMMARY OF THE INVENTION

In accordance with the present invention, the presence of microorganisms in a liquid sample can be determined by a method comprising the steps of (a) filtering the liquid sample through a filter having a pore size which is small enough to prevent passage of microorganisms through the filter but large enough to permit passage of any free reducing agents present in the sample whereby microorganisms present in the sample are retained on the filter;

(b) passing a test solution comprising a chromogenic reagent through the filter having the retained microorganisms thereon, said chromogenic reagent having an oxidation potential such that the reagent can be reduced by microbial dehydrogenase and said chromogenic reagent being selected such that reduction of the chromogenic reagent yields a visibly colored product; and (c) monitoring the filter for the formation of a visibly colored product, wherein the formation of a visibly colored product is indicative of the presence of microorganisms in the sample. This method can be practiced with the aid of a kit which is also an aspect of the invention.

Either the method or the kit of the invention may be particularly adapted for the detection of Gram-negative bacteria. In this case, a combination of a non-ionic alkyl glucoside-type surfactant and a chaotropic agent is added to the sample before filtration or included as a sterile wash solution which is passed through the filter after the sample and before the chromogenic reagent.

DETAILED DESCRIPTION OF THE INVENTION

Figure 1:
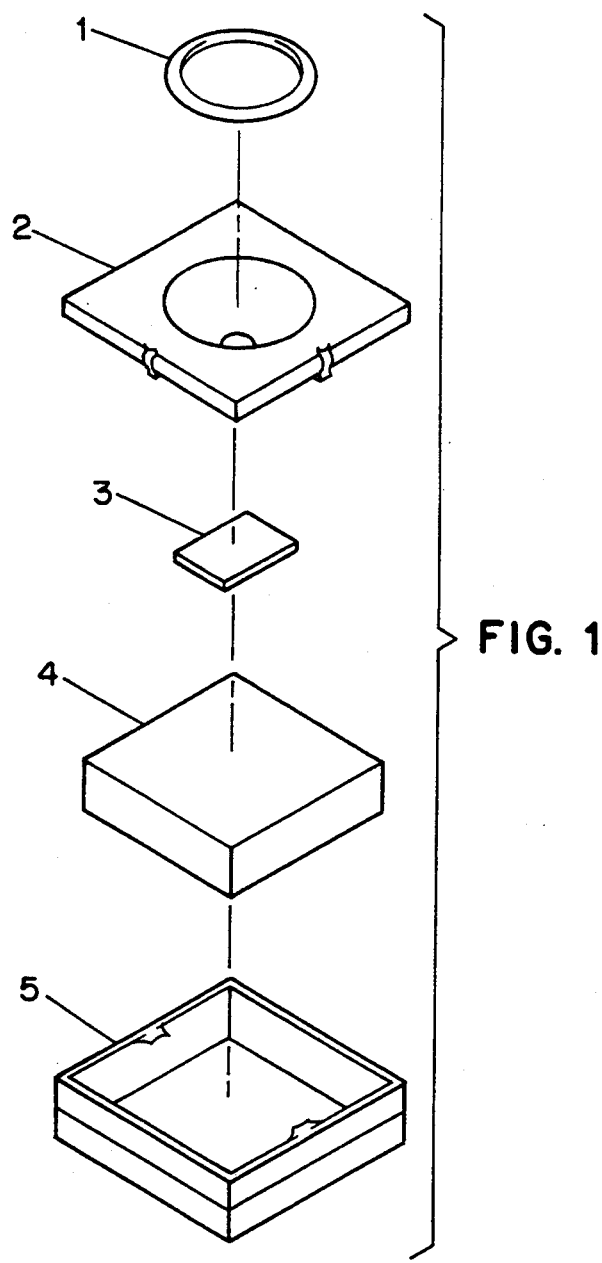
FIG. 1 shows an exploded view of a first apparatus useful in practicing the present invention.

The present invention provides a highly effective means for detecting the presence of microorganisms, particularly bacteria and more particularly Gram-negative bacteria, directly from biological samples. The method is particularly applicable for use with samples of urine, blood, milk and water. The method can also be used on samples of process solutions, i.e., in the wood and pulp industry, the sugar industry or urban waste water, and other liquid samples in which the presence of microorganisms is of interest.

As used herein, the term "microorganism" refers to bacteria and yeasts.

In its simplest form, the method of the invention involves a three step process: filtering the sample, adding the test solution, and observing the result. The filtration step is performed by passing the liquid sample through a filter having a pore size which retains microorganisms on the filter but allows any free reducing compounds which may be present to pass through the filter. Examples of free reducing compounds that may be present include soluble enzymes, ascorbic acid, pharmaceutical compounds and low molecular weight sulfhydryl-containing molecules such as glutathione. Suitable filters for this purpose are depth filters made up of randomly stratified fibres, and having a pore size from 0.75 to about 1.2 $\mu$m. Such matrix materials include, but are not intended to be limited to, cotton, glass fiber, woven materials as cloth, nylon, or other polymeric material. Bacteria, although being less than 1 $\mu$m size are entrapped on and into the filter by mechanical retention.

After filtration to separate microorganisms in the sample from any free reducing compounds present in the sample, a test solution containing a chromogenic reagent is added and drawn through the filter. The chromogenic reagent can be essentially any material having an oxidation potential such that it can be reduced by microbial dehydrogenase to produce a colored product. Preferred reagents are those that are most rapidly reduced and those that produce the most intensely colored products. Suitable chromogenic reagents include tetrazolium salts, such as triphenyltetrazolium chloride, iodonitratetrazolium, neotetrazolium chloride, blue tetrazolium and nitroblue tetrazolium; and other materials such as methylene blue, dichloroindophenol and resazurin.

The test solution may also contain an electron transfer mediator effective to accelerate and amplify the hydrogenation reaction. Suitable mediators include phenazine methosulphate (PMS), menadione, meldola blue (C.I. 51175, Basic Blue 6) and methoxy phenazine methosulfate.

Passing the test solution through the filter causes microorganisms on the filter to be "dyed," making them immediately detectable. For example, a light yellow solution of NBT when reduced forms a visible, blue, formazane precipitate with considerable rapidity on the filter if living microorganisms are present. Indeed, NBT is a preferred chromogenic reagent for use in the invention as the blue color of reduced NBT is formed considerably more rapidly than the red of TTC and is easier to distinguish from the red color of samples containing hemoglobin.

NBT and MTT are equally rapid from the point of view of color formation, but the advantage of NBT in comparison with MTT is that the color can be deposited on a restricted area of the filter because it precipitates at the point where the dehydrogenases are situated around the bacteria. Excess NBT does not dissolve the blue formazane. Using NBT bacteria can be identified with rapidity at room temperature by visual inspection and without any separate measuring equipment. MTT is water-soluble and thus is not retained on the fiber but it can be used in spectrophotometric methods.

The amount of chromogenic reagent present in the test solution is not critical, e.g. NBT from 0.2 mg/ml to 2.0 mg/ml are suitable and depends on the speed with which the reagent is reduced, (which controls the amount of product produced), NBT and MTT being rapid and leading to high extinction coefficient of the reduced product (i.e. the intensity of the color produced) and to the level of sensitivity required. The speed of the reduction can be varied by the addition of an accelerator. In general, test solutions containing from 0.2 mg/ml to 2.0 mg/ml of chromogenic reagent and 0.1 to 10 g/l of an accelerator such as PMS are suitable.

The basic method of the invention can be modified in several ways to adapt to certain special circumstances. For example, for samples which may contain leucocytes or other cells which can themselves reduce the chromogenic reagent but which are not of interest in the assay, a prefiltration step may be added. Suitable prefilters have a pore size of 10 to 20 μm which retains leucocytes and other mammalian cells but permits passage of yeast and bacteria.

A washing step may also be added between the filtration step and the addition of the test solution. This washing, can be performed with buffer to further remove erroneous results caused by free-reducing compounds.

If Gram-negative bacteria are of special interest, the sample itself or the washing buffer can be modified to inhibit the dehydrogenase enzymes of all but Gram-negative bacteria. This is done using a non-ionic alkyl glucoside-type detergent, for example octyl glucoside or octyl maltoside, and a chaotropic compound such as guanidine or urea. Other non-ionic detergents such as Triton X-100 and Tween 80, which are polyxyethelyne compounds, have no effects under the same conditions, as was reported much earlier by Dakay et al. (1981).

If present in the sample solution or in the wash buffer, the non-ionic alkyl glucoside detergent is suitably used at a concentration of from 8 mg/ml to 12 mg/ml.

Chaotropic compounds are suitably used at concentrations of from 0.5 to 1.0M in the sample solution or in the wash buffer.

The method of the invention can be practiced using any filtration device, including laboratory devices in which vacuum is used to draw liquid through the filter. For use in a kit, however, a filter apparatus in which an absorbent material is disposed on one side of the filter to draw liquid through the filter is more convenient. Two apparatus of this type are shown in FIGS. 1 and 2.

Figure 2:
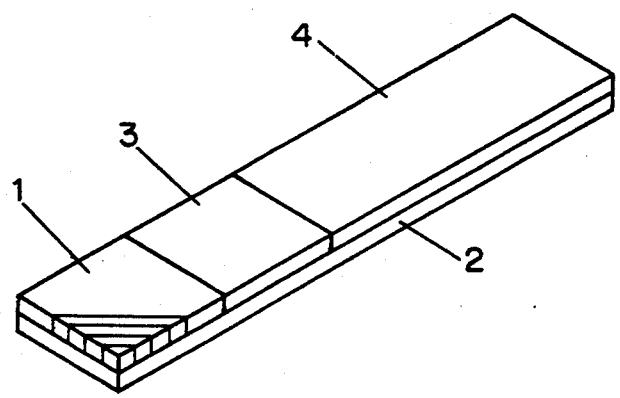
FIG. 2 shows a second apparatus useful in practicing the present invention.

FIG. 1 presents an exploded view of an apparatus in which a liquid sample e.g. urine is pipetted onto the prefilter 1 if the sample is particulate or if it contains large numbers of leucocytes (in other cases prefiltration is not necessary). In the collection chamber 2 the microbes in the sample are trapped on the filter 3. The sample is prebuffered or washed with a buffer solution after filtration the sample to detect all microbes.

To detect only the gram-negative bacteria the detergents are added to the sample with the buffer solution or to the wash solution.

After filtration the bacteria are visualized by detecting their own dehydrogenases which form blue formazane precipitate on the filter. Below the filter 3 is an adsorbent material 4, which absorbs the sample liquid. All the parts of the apparatus takes the form of a small box.

The apparatus depicted in FIG. 2 includes a prefilter 1 for removing particles from the sample, a filter 3 on which bacteria are trapped and an adsorbent material 4 which may be attached e.g. using two-sided tape to the base 5. The buffered sample is adsorbed firstly to the prefilter when dipping the edge of filter 1 to the buffered sample solution. The particulate matter or leucocytes in the sample are retained on the filter 1 and bacteria present in the sample will move to the interface between prefilter 1 and filter 3, and the liquid part of the sample will penetrate filter 3 and possibly to the adsorbent material 4. The bacteria can be demonstrated by dipping the edge of prefilter 1 to the chromogenic solution and blue formazane due to bacterial own dehydrogenases is produced around the bacteria. If only gram-negative bacteria are visualized the detergents maybe added to the buffered sample and to the chromogenic solution.

EXAMPLE 1

In the following examples, The test bacteria were types isolated from urinary tract infections, either ATCC type strains or clinical strains obtained from the Department of Serobiology of the University of Helsinki. The Gram-negative bacteria were *Escherichia coli* (ATCC 25922 and several clinical strains): *Klebsiella aerogenes* (ATCC 13833), *Proteus mirabilis*, *Pseudomonas aeruginosa* and *Enterobacter aerogenes* (ATCC 13048). Gram-positive strains included *Staphylococcus aureus* (ATCC 25923), *Staphylococcus saprophyticus*, *Staphylococcus epidermidis*, *Streptococcus agalactiae*, *Streptococcus faecium* (ATCC 9790), β-hemolytic Streptococcus, group B, Enterococcus sp. and Corynebacterium sp. The yeast strains were *Candida albicans* ATCC 28367 and 36802. The bacteria were cultivated overnight in BHI broth (Brain-Heart Infusion, Difco, Detroit) at 37° C. and the bacterial count in the broth was adjusted to about $10^8$ CFU/ml (colony forming units/ml) by dilution with sterile 0.9% sodium chloride solution to an optical density of 0.400 at 650 mm (Perkin Elmer Spectrophotometer, Norwalk). The bacterial population was checked by dilution and plating on blood agar. The yeast strains were cultivated for 2 days at 37° C. on Sabouraud agar plates and suspensions of $10^8$ CFU/ml were made by transferring microbial mass to sterile salt solution to an optical density of 0.400 as described above. In addition to these samples, 100 urine samples were collected. The bacterial contents of these samples were assayed by bacterial cultivation (Uricult®, Orion Diagnostica). Leucocytes possibly present in the samples were collected on a leucocyte filter (Pall Biosupport Company, Glen Cove).

In the assay 100 μl of bacterial suspension was added to 100 μl 0.2M Tris-HCL buffer, pH 6.5, 7.2 or 8.5 (Sigma, St. Louis) containing 1.0% glucose (BDH, Poole) or fructose (BDH, Poole), acetate (Merck, Darmstadt) or glutamate (Merck, Darmstadt). For some assays the mixture also contained varying amounts of octyl glucoside (Sigma, St. Louis) or guanidine hydrochloride (BDH, Poole) and was incubated for different times on a 96-place well plate. The sample was pipetted to a filtering apparatus, on which the bacteria were collected in an area of about 3 mm diameter on the surface of the filter (Schleicher and Schuell glass fiber filter No. 8), or the filter (leucocyte filter, Pall BioSupport Company, Glen Cove) was dipped into the sample and the bacteria passed through it and transferred to the filter interface where another filter (Schleicher and Schuell No. 8) was positioned. The bacteria were detected by adding 100 μl NBT-solution (1 mg/ml, Sigma, St. Louis) containing 10 μl PMS (1 mg/ml, Sigma, St. Louis) to the filter.

Color formation was estimated visually after different times according to the scale:
0 = colorless
1 = weak color
2 = clearly detectable color
3 = strongly colored
4 = darkly colored
5 = very darkly colored

EXAMPLE 2

Detection of micro-organisms at different concentrations was carried out as described in Example 1. The micro-organisms were incubated for a short time on a shaker and then for 30 seconds in 0.2M Tris-HCL buffer containing 1.0% glucose, at different pH values. The suspension was then transferred to a filter, to which a solution of NBT-PMS was added and the blue color due to production of formazane was read after 30 minutes. The results are summarized in Table 1.

TABLE 1

| Test bacteria, CFU/ml | | pH 6.5 | pH 7.2 | pH 8.5 |
|---|---|---|---|---|
| E. Coli (ATCC 25922) | $10^7$ | 2 | 3 | 3 |
|  | $10^6$ | 2 | 2 | 2 |
|  | $10^5$ | 0 | 0 | 0 |
| E. Coli a | $10^7$ | 4 | 4 | 3 |
|  | $10^6$ | 2 | 2 | 2 |
|  | $10^5$ | 0 | 0 | 0 |
| E. Coli b | $10^7$ | 4 | 4 | 4 |
|  | $10^6$ | 0 | 2 | 3 |
|  | $10^5$ | 0 | 0 | 0 |
| E. Coli 2956 | $10^7$ | 2 | 3 | 1 |
|  | $10^6$ | 1 | 1 | 1 |
|  | $10^5$ | 0 | 0 | 0 |
| E. Coli 3338 | $10^7$ | 4 | 5 | 5 |
|  | $10^6$ | 2 | 2 | 2 |
|  | $10^5$ | 0 | 0 | 0 |
| E. Coli 110515 | $10^7$ | 2 | 3 | 3 |
|  | $10^6$ | 2 | 2 | 2 |
|  | $10^5$ | 0 | 0 | 0 |
| Klebsiella aerogenes (ATCC 13883) | $10^7$ | 5 | 5 | 5 |
|  | $10^6$ | 4 | 4 | 5 |
|  | $10^5$ | 2 | 3 | 3 |
| Enterobacter aerogenes (ATCC 13883) | $10^7$ | 5 | 5 | 5 |
|  | $10^6$ | 4 | 5 | 5 |
|  | $10^5$ | 3 | 3 | 3 |
| Proteus mirabilis | $10^7$ | 5 | 5 | 5 |
|  | $10^6$ | 3 | 3 | 4 |
|  | $10^5$ | 1 | 1 | 2 |
| Pseudomonas aeruginosa | $10^7$ | 4 | 4 | 4 |
|  | $10^6$ | 2 | 2 | 2 |
|  | $10^5$ | 1 | 2 | 2 |
| Enterococcus sp. | $10^7$ | 5 | 5 | 5 |
|  | $10^6$ | 3 | 3 | 3 |
|  | $10^5$ | 2 | 2 | 2 |
| Streptococcus agalactia | $10^7$ | 5 | 5 | 5 |
|  | $10^6$ | 3 | 2 | 3 |
|  | $10^5$ | 1 | 2 | 1 |
| Streptococcus beta-hemol. B | $10^7$ | 5 | 5 | 5 |
|  | $10^6$ | 3 | 4 | 4 |
|  | $10^5$ | 1 | 2 | 2 |
| Streptococcus faecium (ATCC 9790) | $10^7$ | 4 | 4 | 4 |
|  | $10^6$ | 3 | 3 | 3 |
|  | $10^5$ | 1 | 2 | 2 |
| Staphylococcus aureus | $10^7$ | 3 | 5 | 5 |
|  | $10^6$ | 2 | 3 | 3 |
|  | $10^5$ | 0 | 1 | 2 |
| Staphylococcus epidermidis | $10^7$ | 4 | 4 | 4 |
|  | $10^6$ | 2 | 2 | 3 |
|  | $10^5$ | 0 | 1 | 2 |

EXAMPLE 3

Different clinical strains of Escherichia coli were detected on the filter at different concentrations. The bacteria were incubated for 30 seconds in 0.2M Tris-HCL buffer, pH 7.2 containing 1.0% glucose and transferred to a filter to which NBT-PMS solution was added and the intensity of the blue color of formazane was estimated after 30 minutes. The results are shown in Table 2.

TABLE 2

| Bacterial strain | CFU/ml | | | | |
|---|---|---|---|---|---|
|  | $10^9$ | $10^8$ | $10^7$ | $10^6$ | $10^5$ |
| E. coli a | 5 | 5 | 4 | 2 | 0 |
| E. coli b | 5 | 4 | 3 | 2 | 0 |
| E. coli 2956 | 4 | 4 | 3 | 1 | 0 |
| E. coli 3338 | 5 | 5 | 5 | 2 | 0 |
| E. coli 110515 | 4 | 4 | 3 | 0 | 0 |

EXAMPLE 4

The ability of guanidine to prevent formazane production by a Gram-positive bacterium, Staphylococcus saprophyticus, versus the effect on the Gram-negative E. coli was determined. The test was performed as in Example 2 and with the addition of 0.5M guanidine.

The results are shown in Table 3. As can be seen from Table 3, guanidine at this concentration essentially eliminated the formazane producing activity of the Gram-positive organism.

TABLE 3

| Test bacteria, CFU/ml | | No Additives | | | Guanidine | | |
|---|---|---|---|---|---|---|---|
| | | pH | | | | | |
| | | 6.5 | 7.2 | 8.5 | 6.5 | 7.2 | 8.5 |
| E. Coli (ATCC 25922) | $10^7$ | 2 | 3 | 3 | 2 | 3 | 3 |
| | $10^6$ | 2 | 2 | 2 | 2 | 2 | 2 |
| | $10^5$ | 0 | 0 | 0 | 0 | 0 | 0 |
| Staphylococcus | $10^7$ | 4 | 4 | 4 | 0 | 0 | 1 |
| saprophyticus | $10^6$ | 0 | 2 | 3 | 0 | 0 | 0 |
| | $10^5$ | 0 | 0 | 0 | 0 | 0 | 0 |

EXAMPLE 5

Prevention of formazane production by different bacteria with 0.5M guanidine at pH 7.2, in the presence of different substrates (1% glucose; 1% fructose; 1% glutamate; acetate) was studied. In other respects the test was carried out as in the case of Example 1. The results shown in Table 4, indicated that contrary to the initial expectation raised by Example 4, guanidine alone cannot generally be used to selectively inhibit formazane production by Gram-positive organisms.

TABLE 4

| Test bacteria, CFU/ml | | gluc. | fruct. | glutam | acet. |
|---|---|---|---|---|---|
| GRAM − | $10^7$ | 5 | 5 | 4 | 3 |
| Escherichia coli a | $10^6$ | 4 | 4 | 3 | 2 |
| GRAM + Streptococcus, | $10^7$ | 5 | 5 | — | 5 |
| Group B, 102 | $10^6$ | 2 | 2 | — | 1 |
| GRAM − | $10^7$ | 5 | 5 | — | 5 |
| Klebsiella aerogenes | $10^6$ | 4 | 4 | — | 0 |
| (ATCC 13883) | | | | | |
| GRAM + Streptococcus, | $10^7$ | 4 | 4 | — | 2 |
| faecium (ATCC 9790) | $10^6$ | 0 | 0 | — | 0 |
| GRAM − | $10^7$ | 5 | 5 | — | 5 |
| Enterobacter sp. | $10^6$ | 4 | 4 | — | 3 |
| GRAM + Staphylococcus | $10^7$ | 3 | 3 | — | 3 |
| epidermidis | $10^6$ | 0 | 0 | — | 0 |
| GRAM − Proteus mirabilis | $10^7$ | 5 | 5 | — | 5 |
| | $10^6$ | 3 | 3 | — | 3 |
| GRAM + Enterococcus, sp. | $10^7$ | 5 | 5 | — | 2 |
| | $10^6$ | 0 | 0 | — | 0 |
| GRAM − Pseudomonas | $10^7$ | 0 | 0 | 3 | 0 |
| aeruginosa | $10^6$ | 0 | 0 | 2 | 0 |
| GRAM + Staphylococcus | $10^7$ | 5 | 5 | 3 | 5 |
| aureus | $10^6$ | 1 | 1 | 3 | 2 |
| GRAM + saprophyticus | $10^7$ | 3 | 3 | 0 | 2 |
| | $10^6$ | 0 | 0 | 0 | 0 |

EXAMPLE 6

Prevention of formazane production by different bacteria with octyl glucoside at different concentrations was studied. In other respects the test was carried out as in the case of Example 1 in the presence of 1% glucose. The bacterial concentration was $10^7$ CFU/ml. for all experiments. The results are shown in Table 5.

TABLE 5

| | Octylglucoside Concentration (g/l) | | | |
|---|---|---|---|---|
| | 4 | 6 | 8 | 10 |
| GRAM − | | | | |
| Escherichia coli a | 4 | 5 | 4 | 4 |
| Klebsiella aerogenes | 5 | 5 | 5 | 5 |
| Enterobacter aerogenes | 5 | 5 | 5 | 3 |
| Proteus mirabilis | 5 | 2 | 2 | 2 |
| Pseudomonas aeruginosa | 0 | 0 | 0 | 0 |
| GRAM + | | | | |
| Staphylococcus aureus | 5 | 0 | 0 | 0 |
| Enterococcus sp. | 4 | 0 | 0 | 0 |
| Staphylococcus epidermidis | 3 | 3 | 0 | 0 |
| Staphylococcus saprophyticus | 3 | 2 | 2 | 2 |
| Streptococcus agalactiae | 4 | 0 | 0 | 0 |
| Streptococcus faecium | 3 | 0 | 0 | 0 |

TABLE 5-continued

| | Octylglucoside Concentration (g/l) | | | |
|---|---|---|---|---|
| | 4 | 6 | 8 | 10 |
| Streptococcus sp. B | 5 | 0 | 0 | 0 |

EXAMPLE 7

Prevention of formazane production by different bacteria using 0.5M guanidine with and without 10 g/l octyl glucoside in the presence of 1% glucose. In other respects the test was performed as in the case of Example 1. The bacterial concentration was $10^7$ CFU/ml for each experiment. As shown in Table 6, the combination of chaotropic agent and the nonionic glucoside surfactant provides substantially complete specificity between Gram-positive and Gram-negative bacteria, and also pseudomonas becomes usable, whereas the yeasts are not stained.

TABLE 6

| | octyl glucoside added | octyl glucoside not added |
|---|---|---|
| GRAM − | | |
| Escherichia coli a | 4 | 5 |
| Klebsiella aerogenes | 4 | 5 |
| Enterobacter aerogenes | 4 | 5 |
| Proteus mirabilis | 5 | 5 |
| Pseudomonas aeruginosa | 4 | 0 |
| GRAM + | | |
| Staphylococcus aureus | 0 | 5 |
| Enterococcus sp. | 0 | 5 |
| Staphylococcus epidermidis | 0 | 4 |
| Staphylococcus saprophyticus | 0 | 4 |
| Streptococcus agalactiae | 0 | 5 |
| Streptococcus faecium | 0 | 4 |
| Streptococcus sp. B | 1 | 5 |
| Corynebacterium sp. | 0 | 5 |
| Candida albicans | 0 | 4 |
| Candida albicans B | 0 | 3 |

EXAMPLE 8

100 urine samples were analyzed with Uricult ® and with the method described in Example 2, in which bacteria were detected with the aid of formazane. A positive result (+) of the Uricult ® test indicates that the sample contains at least $10^5$ bacteria/mi. Bacterial counts below $10^5$ CFU/ml give a negative result (−). A positive result with formazane was recorded when the color intensity was 2 or greater and a negative result was indicated by a color intensity of 0 or 1. The results of this comparison, shown in Table 7, indicate that tests results with the claims method are of comparable reliability of the commercial product.

TABLE 7

| Standard Test Type | Result | formation of formazane | |
|---|---|---|---|
| | | + | − |
| Total bacterial count, | + | 21 | 0 |
| Uricult | − | 0 | 79 |
| GRAM − reaction, | + | 12 | 1 |
| | − | 0 | 87 |
| Gram + reaction, | + | 6 | 2 |
| | − | 0 | 92 |

We claim:

1. A method for the selective detection of Gram negative bacteria in a liquid sample, comprising the steps of:

(a) adding a non-ionic alkyl glucoside detergent and a chaotropic compound to the sample;

(b) filtering the liquid sample through a filter having a pore size which is small enough to prevent passage of microorganisms through the filter but large enough to permit passage of any free reducing compounds present in the sample, whereby microorganisms present in the sample are retained on the filter;

(c) passing a test solution comprising a chromogenic reagent, in an amount effective to detect the Gram negative bacteria in the liquid sample, through the filter having the retained microorganisms thereon, said chromogenic reagent having an oxidation potential such that the reagent can be reduced by microbial dehydrogenase and said chromogenic reagent being selected such that reduction of the chromogenic reagent yields a colored product; and (d) monitoring the filter for the formation of a colored product, wherein the formation of a colored product is indicative of the presence of Gram-negative bacteria in the sample.

2. A method for the selective detection of Gram negative bacteria in a liquid sample, comprising the steps of:

(a) filtering the liquid sample through a filter having a pore size which is small enough to prevent passage of microorganisms through the filter but large enough to permit passage of any free reducing compounds present in the sample, whereby microorganisms present in the sample are retained on the filter;

(b) washing the microorganisms retained on the filter with a detergent solution comprising a non-ionic alkyl glucoside detergent and a chaotropic compound;

(c) passing a test solution comprising a chromogenic reagent, in an amount effective to detect the Gram negative bacteria in the liquid sample, through the filter having the retained microorganisms thereon, said chromogenic reagent having an oxidation potential such that the reagent can be reduced by microbial dehydrogenase and said chromogenic reagent being selected such that reduction of the chromogenic reagent yields a colored product; and (d) monitoring the filter for the formation of a colored product, wherein the formation of a colored product is indicative of the presence of Gram-negative bacteria in the sample.

3. A method according to claim 1 or 2, wherein the chromogenic reagent is a tetrazolium salt.

4. A method according to claim 3, wherein the chromogenic reagent is selected from the group consisting of triphenyltetrazolium chloride, iodonitrotetrazolium, neotetrazolium chloride, blue tetrazolium and nitroblue tetrazolium.

5. A method according to claim 1 or 2, wherein the chromogenic reagent is selected from the group consisting of methylene blue, dichloroindophenol and resazurin.

6. A method according to claim 1 or 2, wherein the pore size of the filter is from 0.75 to 1.2 microns.

7. A method according to claim 1 or 2, wherein the chaotropic compound is guanidine or urea.

8. A method according to claim 7, wherein the detergent is octylglucoside or octylmaltoside.

9. A method according to claim 1 or 2, wherein the detergent is octylglucoside or octylmaltoside.

10. A method according to claim 1 or 2, wherein the chromogenic reagent is a tetrazolium salt.

11. A method according to claim 1 or 2, wherein the chromogenic reagent is selected form the group consisting of triphenyltetrazolium chloride, iodonitrotetrazolium, neotetrazolium chloride, blue tetrazolium and nitroblue tetrazolium.

12. A method according to claim 1 or 2, wherein the chromogenic reagent is selected form the group consisting of methylene blue, dichloroindophenol and resazurin.

13. A method according to claim 1 or 2, wherein the chaotropic compound is guanidine or urea.

14. A method according to claim 1 or 2, wherein the liquid sample is urine.

15. A test kit for the detection of Gram negative bacteria in a liquid sample comprising, in packaged combination, (a) a filter apparatus comprising a filter having a pore size which is small enough to prevent passage of microorganisms through the filter but large enough to permit passage of any free reducing agents present in the sample whereby microorganisms present in the sample are retained on the filter and means for drawing the liquid sample through the filter;

(b) a test solution comprising a chromogenic reagent, said chromogenic reagent having an oxidation potential such that the reagent can be reduced by microbial dehydrogenase and said chromogenic reagent being selected such that reduction of the chromogenic reagent yields a colored product; and (c) a sterile wash solution comprising a non-ionic alkyl glucoside detergent and a chaotropic agent.

16. A test kit according to claim 15, wherein the filter apparatus further comprises prefiltering means having a pore size which permits passage of microorganisms but retains mammalian cells and particulate materials present in the liquid sample.

17. A test kit according to claim 15, wherein the means for drawing liquid through the filter is a layer of adsorbent material disposed in contact with the filter.

18. A test kit according to claim 15, wherein the pore size of the filter is from 0.75 to 1.2 microns.

* * * * *